United States Patent
Rao et al.

(10) Patent No.: US 8,212,092 B2
(45) Date of Patent: *Jul. 3, 2012

(54) PROCESS FOR THE REDUCTION OF ACIDIC CONTAMINATES IN FLUORINATED HYDROCARBONS

(75) Inventors: Velliyur Nott Mallikarjuna Rao, Wilmington, DE (US); Allen C Sievert, Elkton, MD (US)

(73) Assignee: E I du Pont de Nemours and Company, Wilmington, DE (US)

( * ) Notice: Subject to any disclaimer, the term of this patent is extended or adjusted under 35 U.S.C. 154(b) by 93 days.

This patent is subject to a terminal disclaimer.

(21) Appl. No.: 12/144,394

(22) Filed: Jun. 23, 2008

(65) Prior Publication Data

US 2008/0255396 A1    Oct. 16, 2008

Related U.S. Application Data

(63) Continuation of application No. 10/444,487, filed on May 23, 2003, now Pat. No. 7,405,334.

(51) Int. Cl.
*C07C 17/38* (2006.01)
(52) U.S. Cl. .................................... 570/177; 570/179
(58) Field of Classification Search .................. None
See application file for complete search history.

(56) References Cited

U.S. PATENT DOCUMENTS

| 2,888,494 | A | * | 5/1959 | Kissling | 570/239 |
| 4,102,981 | A | * | 7/1978 | Woychesin et al. | 423/240 R |
| 5,684,211 | A | | 11/1997 | Kawai | |
| 6,187,976 | B1 | | 2/2001 | Van Der Puy et al. | |
| 7,405,334 | B2 | * | 7/2008 | Rao et al. | 570/177 |
| 2001/0000911 | A1 | | 5/2001 | Stewart et al. | |

FOREIGN PATENT DOCUMENTS

| GB | 1 346 936 | 2/1974 |
| WO | WO 95/26218 | 10/1995 |
| WO | WO 96/35653 | 11/1996 |
| WO | WO 98/00378 | 1/1998 |

OTHER PUBLICATIONS

Lewis, Sr. Hawley'S Condensed Chemical Dictionary, Twelth Edition, 1993, p. 531.

* cited by examiner

*Primary Examiner* — Rosalynd Keys

(57) ABSTRACT

The present invention relates to processes for reducing the concentration of acidic impurities HF, HCl, HBr, HI, $HNO_3$ and $H_2SO_4$ in fluorinated hydrocarbons. The process involves: (i) contacting the fluorinated hydrocarbon with a phosphorous oxyacid salt, and (ii) recovering the fluorinated hydrocarbon having reduced concentration of, or substantially free of, said acidic contaminant, provided that said fluorinated hydrocarbon is not $CF_3CH_2CF_3$ or $CF_3CHFCF_3$.

11 Claims, No Drawings

PROCESS FOR THE REDUCTION OF ACIDIC CONTAMINATES IN FLUORINATED HYDROCARBONS

CROSS-REFERENCE TO RELATED APPLICATION

This application is a Continuation of application Ser. No. 10/444,487 filed May 23, 2003.

BACKGROUND OF THE INVENTION

1. Field of the Invention

The present invention relates to a process for reducing the concentration of acidic contaminates in fluorinated hydrocarbons by contact with a phosphorous oxyacid salt.

2. Description of Related Art

Chlorine- and bromine-substituted fluorinated hydrocarbons have long found applications as refrigerants, blowing agents, propellants, solvents, and fire extinguishants. However, dissociation of these materials in the atmosphere has been linked to depletion of stratospheric ozone. Many of these materials have been replaced by fluorinated hydrocarbons that contain only carbon, hydrogen, and fluorine (i.e., hydrofluorocarbons or HFC's). Examples of such hydrofluorocarbons include 1,1,1,2,3,3,3-heptafluoropropane ($CF_3CHFCF_3$ or HFC-227ea, an aerosol propellant and fire extinguishant), 1,1,1,3,3,3-hexafluoropropane ($CF_3CH_2CF_3$ or HFC-236fa, a fire extinguishant and refrigerant), 1,1,1,3,3-pentafluoropropane ($CF_3CH_2CHF_2$ or HFC-245fa, a polymer foam blowing agent), and 1,1,1,2-tetrafluoroethane ($CF_3CH_2F$ or HFC-134a, a refrigerant and aerosol propellant).

Commercial manufacturing processes for hydrofluorocarbons often involve addition of HF, an inorganic acid, to olefins. For example, HFC-227ea is prepared by addition of HF to hexafluoropropane (see U.S. Pat. No. 6,281,395). Other processes involve reacting HF with chlorinated hydrocarbons such as chloroolefins, chloroalkanes, or partially fluorinated chlorocarbons. For example, HFC-236fa is prepared by reacting HF with 1,1,1,3,3,3-hexachloropropane and HFC-245fa is prepared by reacting HF with 1,1,1,3,3-pentachloropropane (see U.S. Pat. No. 6,291,730). In this type of exchange process, HCl, an inorganic acid, is formed as a by-product of the substitution of fluorine for chlorine. Other hydrofluorocarbon manufacturing processes involve replacement of a chlorine substituent in a chlorofluorocarbon or a hydrochlorofluorocarbon with a hydrogen substituent by reaction with hydrogen with elimination of HCl. For example, HFC-134a is prepared by reaction of hydrogen with 1,1-dichloro-1,2,2,2-tetrafluoroethane (see U.S. Pat. No. 5,208,397) and HFC-236fa is prepared by reaction of hydrogen with 2,2-dichloro-1,1,1,3,3,3-hexafluoropropane (see International Patent Application No. 96/17,813).

Fluoroolefins such as hexafluoropropane ($C_3F_6$, HFP) and 1,1,3,3,3-pentafluoro-1-propene ($CF_3CH=CF_2$, HFC-1225zc) are another class of fluorinated hydrocarbons of commercial interest; these compounds are often useful as polymer intermediates. Fluoroolefins may be prepared under conditions where acidic contaminants may be present. For example, U.S. Pat. No. 5,057,634 discloses a process for preparation of hexafluoropropane comprising as a final step hydrodehalogenating $CF_3CClFCF_3$ in the presence of hydrogen and a catalyst. U.S. Pat. No. 6,093,859 discloses a process for producing HFC-1225zc involving dehydrofluorinating HFC-236fa at an elevated temperature in the vapor phase over a catalyst.

The crude product in the aforementioned processes may be contaminated with hydrogen chloride (HCl) and/or hydrogen fluoride (HF). Removal of HCl and HF is usually accomplished by distillation, but traces of these acidic contaminants often remain in the product. Even after distillation, fluorinated hydrocarbons may remain contaminated with HF or HCl due to the formation of azeotropes or azeotrope-like compositions; that is constant-boiling mixtures that behave as a single substance. For example, it has been disclosed that HFC-227ea forms an azeotrope with HF (see U.S. Pat. No. 6,376,272) and HFC-236fa forms an azeotrope with HF (see U.S. Pat. No. 5,563,304). These acidic contaminants must be removed from the hydrofluorocarbons prior to commercial use.

It is well-known that acidic contaminants in perhalogenated fluorocarbons (e.g., $CCl_2F_2$) may be removed by treatment with a strong base such as sodium hydroxide without degradation of the perhalogenated fluorocarbon. However, substitution of one or more hydrogen substituents in a saturated hydrocarbon by a halogen (i.e., fluorine, chlorine, bromine, or iodine) often increases the acidity of at least some of the remaining hydrogen substituents (see the discussion by Reutov, Beletskaya, and Butin on pages 51 to 58 in CH-Acids, Pergamon Press, Oxford, (1978)). Depending on the particular arrangement of hydrogen and halogen substituents, exposure of a saturated partially halogenated hydrocarbon to a base such as sodium hydroxide may result in facile elimination of the corresponding hydrogen halide from the halogenated hydrocarbon by dehydrohalogenation, which is the elimination of hydrogen halide from a saturated halogenated hydrocarbon to produce an unsaturated halogenated compound. The unsaturated compound so formed can be acyclic (linear or branched) or cyclic, depending upon the starting halogenated hydrocarbon.

Therefore, removal of acidic contaminants from saturated halogenated hydrocarbons by contacting mixtures of saturated halogenated hydrocarbons and HF or HCl with strong bases, such as sodium hydroxide, potassium hydroxide, sodium carbonate, or potassium carbonate, may result in the formation of substantial amounts of unsaturated compounds (e.g., amounts greater than 5 weight percent of the starting halogenated hydrocarbon) due to elimination of hydrogen halide through dehydrohalogenation. For example, as disclosed in the examples herein, contact of HFC-227ea with strong base gives some hexafluoropropane, contact of HFC-236fa with strong base gives some 1,1,3,3,3-pentafluoro-1-propene, contact of HFC-245fa with strong base gives some 1,3,3,3-tetrafluoro-1-propene, contact of 2,3-dichloro-1,1,1,3,3,3-pentafluoropropane ($CF_3CHClCClF_2$, HCFC-225da) with strong base gives some 2-chloro-1,1,3,3,3-pentafluoro-1-propene, and contact of 1,1,1,2,2,3,4,5,5,5-decafluoropentane ($CF_3CF_2CHFCHFCF_3$, HFC-43-10mee) with strong base gives some nonafluoropentenes.

U.S. Pat. No. 6,187,976 example 5 discloses a liquid phase fluorination process for $CCl_3CH_2CCl_3$. The product stream consisting of HCFC-235fa (1-chloro-1,1,3,3,3-pentafluoropropane), HFC-236fa (1,1,1,3,3,3-hexafluoropropane), 1,1,3,3,3-pentafluoropropene, HF, HCl, and other minor products is passed through a caustic scrubber. The acid-free product stream contains 25% 1,1,3,3,3-pentafluoropropene.

Because unsaturated fluorocarbons are frequently toxic, their presence in a hydrofluorocarbon product is undesirable. Removal of such unsaturated compounds by distillation is often difficult due to the fact that they may have boiling points close to those of the hydrofluorocarbons or they may even form azeotropes or azeotrope-like mixtures with the hydrofluorocarbons. Thus, formation of unsaturated impurities during a neutralization process is not only a yield loss, but results in the need for additional purification steps which add to the overall cost of the manufacturing process.

Highly fluorinated olefins such as HFP and HFC-1225zc are well-known to be reactive toward nucleophiles (e.g., the anionic portion of a compound such as sodium hydroxide where the hydroxide ion is the nucleophile). Therefore, removal of acidic contaminants from highly fluorinated olefins by contacting mixtures of highly fluorinated olefins and HF or HCl with strong bases, such as sodium hydroxide, potassium hydroxide, sodium carbonate, or potassium carbonate, may result in nucleophilic attack by hydroxide ion at the double bond with hydrolysis (i.e., replacement of the fluoride ion by hydroxide ion) of the olefin and formation of fluoride ions. This can result in a substantial yield loss, such as a yield loss of greater than 5 weight percent of the starting fluorinated olefin. World Intellectual Property Organization patent application publication no. WO 96/29,296 discloses a method for producing fluoroalkanes by high-temperature pyrolysis of chlorodifluoromethane in the presence of an alkane or fluoroalkane. The products of said process are scrubbed with caustic soda prior to isolation (page 3, lines 3, 4, and 5); little fluoroolefins are observed in the products and apparently about 40% of the yield is not to useful products.

There is an industry need for a process to remove acidic contamination from saturated and unsaturated fluorinated hydrocarbons in which the dehydrohalogenation of saturated fluorinated hydrocarbons or hydrolysis of unsaturated fluorinated hydrocarbons is reduced. The present invention meets that need.

BRIEF SUMMARY OF THE INVENTION

The present invention is a process for reducing the concentration of acidic contaminates HF, HCl, HBr, HI, HNO$_3$ and H$_2$SO$_4$ in fluorinated hydrocarbons and involves the steps of: (i) contacting the fluorinated hydrocarbon with a phosphorous oxyacid salt such as orthophosphoric acid salts, phosphorous acid salts, metaphosphoric acid salts, and pyrophosphoric acid salts, and (ii) recovering the fluorinated hydrocarbon having reduced concentration of, or substantially free of, said acidic contaminant, provided that said fluorinated hydrocarbon is not CF$_3$CH$_2$CF$_3$ or CF$_3$CHFCF$_3$. The contacting step of the present process is preferably carried out with the phosphorous oxyacid salt in aqueous solution having a pH of no more than about 10. The present process results in less than about 5 weight percent of the fluorinated hydrocarbon being decomposed by dehydrohalogenation or by hydrolysis during the contacting step and is an improvement over prior art processes for removing such acidic impurities from fluorinated hydrocarbons.

DETAILED DESCRIPTION OF THE INVENTION

This invention provides a process for reducing the amount of acidic contaminants from fluorinated hydrocarbons by contacting acid-contaminated fluorinated hydrocarbons with phosphorous oxyacid salts.

As is well known in the art, when acidic contaminants are contacted with phosphorous oxyacid salts, the acidic contaminant is converted to the corresponding salt. The present inventors have found that when said contacting of the acidic contaminant with the phosphorous oxyacid salts is carried out in the presence of cyclic or acyclic, saturated or unsaturated fluorinated hydrocarbons, reduction or substantial removal of the quantity of acidic contaminant occurs without substantial dehydrohalogenation of the saturated fluorinated hydrocarbon or hydrolysis of the unsaturated fluorinated hydrocarbon. By "without substantial dehydrohalogenation of the saturated fluorinated hydrocarbon" is meant that less than about 5 weight percent of the saturated fluorinated hydrocarbon is converted to an unsaturated fluorinated hydrocarbon. Preferably, less than about 0.5 weight percent of the saturated fluorinated hydrocarbon is converted to an unsaturated fluorinated hydrocarbon. By "without substantial hydrolysis of the unsaturated fluorinated hydrocarbon" is meant that less than about 5 weight percent of the unsaturated fluorinated hydrocarbon is converted to other products by hydrolysis.

Preferably, less than about 0.5 weight percent of the unsaturated fluorinated hydrocarbon is converted to other products by hydrolysis. By "substantial removal" or "substantially free" means that the present process produces a fluorinated hydrocarbon product containing 10 ppm-molar or less, preferably 1 ppm-molar or less, of acidic contaminants.

Phosphorous oxyacid salts of the present invention are: (i) orthophosphoric acid salts of the formula M$_n$H$_{3-n}$PO$_4$, wherein n is an integer from 1 to 3; (ii) phosphorous acid salts of the formula M$_m$H$_{2-m}$(HPO$_3$), wherein m is 1 or 2; (iii) metaphosphoric acid salts of the formula (MPO$_3$)$_z$, wherein z is an integer from 1 to 6; and (iv) pyrophosphoric acid salts of the formula M$_k$H$_{4-k}$P$_2$O$_7$, wherein k is an integer from 1 to 4; wherein M is selected from the group consisting of NH$_4$, Li, Na, and K. Preferred phosphorous oxyacid salts of the present invention are orthophosphoric acid salts of the formula M$_n$H$_{3-n}$PO$_4$, wherein n is an integer from 1 to 3, and M is selected from the group consisting of NH$_4$, Na, and K. Owing to their availability and favorable solubility in water, mixtures of the potassium salts of orthophosphoric acid (K$_3$PO$_4$, K$_2$HPO$_4$, and KH$_2$PO$_4$) are the most preferred phosphorous oxyacid salts. Example salts of orthophosphoric acid include tribasic sodium phosphate (Na$_3$PO$_4$), dibasic sodium phosphate (Na$_2$HPO$_4$), monobasic sodium phosphate (NaH$_2$PO$_4$), tribasic potassium phosphate (K$_3$PO$_4$), dibasic potassium phosphate (K$_2$HPO$_4$), monobasic potassium phosphate (KH$_2$PO$_4$), dibasic ammonium phosphate ((NH$_4$)$_2$HPO$_4$), monobasic ammonium phosphate (NH$_4$H$_2$PO$_4$), tribasic lithium phosphate (Li$_3$PO$_4$), dibasic lithium phosphate (Li$_2$HPO$_4$), monobasic lithium phosphate (LiH$_2$PO$_4$), and their various hydrated salts. Other suitable salts include mixed salts such as for example, sodium ammonium hydrogen phosphate (NH$_4$NaHPO$_4$).

Example salts of pyrophosphoric acid suitable include potassium pyrophosphate (K$_4$P$_2$O$_7$) or sodium pyrophosphate (Na$_4$P$_2$O$_7$) or their mixtures with pyrophosphoric acid. Example salts of metaphosphoric acid include "sodium polyphosphate" (NaPO$_3$)$_p$ or its mixtures with metaphosphoric acid.

Mixtures of any of the aforementioned phosphorous oxyacid salts may also find utility in the present process.

The contacting step of the present invention may be carried out by passing a gaseous or liquid mixture of fluorinated hydrocarbon(s) and acidic contaminant(s) through a bed of substantially dry phosphorous oxyacid salt(s). The salt is consumed in the contacting step and is preferably finely divided to ensure intimate contact with the mixture. In this embodiment, the mixture may be vaporized alone or in combination with an inert carrier gas such as nitrogen. Stirring and agitation of the bed may be carried out through use of known methods.

The contacting step of the present invention may also, and more preferably, be carried out by contacting a gaseous or liquid mixture of fluorinated hydrocarbon(s) and acidic contaminant(s) with an aqueous solution of phosphorous oxyacid salt(s). The concentration of phosphorous oxyacid salts in said aqueous solutions is not critical and is typically from about 1 percent by weight to about 20 percent by weight, preferably from about 3 percent by weight to about 10 percent by weight. Lower concentrations of salts may be volumetrically inefficient in removal of acid contaminants and higher concentrations may tend to form precipitates.

Said aqueous solutions may be prepared by adding the desired quantity(ies) of phosphorous oxyacid salt(s) to water, by adding the desired quantity of a base such as an alkali metal hydroxide to a solution of the phosphorous oxyacid, by adding the desired quantity of phosphorous oxyacid to a solution of alkali metal hydroxide, or by mixing a phosphorous oxyacid with one or more phosphorous oxyacid salts. Other bases, such as ammonia, may be used to neutralize the phosphorous oxyacid.

Preferred aqueous solutions of phosphorous oxyacid salts used in the process of the present invention may have a pH in the range of from about 6 to about 10. Fluorinated hydrocarbons having relatively acidic hydrogen substituents, that is those having acidity constants ($pK_a$) of about 25 or less, may require the use of basic aqueous solutions having a pH in the range of about 6 to about 8, while for less reactive fluorinated hydrocarbons, the pH of the aqueous solution may reach 10 without formation of significant amounts of unsaturated by-products. As illustrated in the present examples, use of aqueous solutions of phosphorous oxyacid salts or other basic salts having a pH greater than 10 may result in a significant conversion of a saturated fluorinated hydrocarbon to an unsaturated compound, or in hydrolysis of an unsaturated fluorinated hydrocarbon. The formation of unsaturated compounds may be detected by analysis of the fluorinated hydrocarbon. In addition, the formation of unsaturated impurities from saturated fluorinated hydrocarbons, as well as the hydrolysis of unsaturated fluorinated hydrocarbons, is accompanied by the appearance of halide ions (e.g., fluoride or chloride) in the recovered aqueous solutions.

Because phosphorous oxyacid salts form buffer solutions, the use of these materials for the process of this invention in the preferred pH range is advantageous compared with use of highly basic compounds (such as sodium hydroxide or potassium hydroxide) in the same pH range, because a high degree of pH monitoring is not necessary.

Acidic contaminants that may be removed from fluorinated hydrocarbons of this invention are the inorganic acids HF, HCl, HBr, HI, $HNO_3$ and $H_2SO_4$. The present process is especially useful for reducing or removing the acidic contaminants HF and HCl, which are often otherwise difficult to remove from fluorinated hydrocarbons. These contaminants arise from previous processing steps which involve these acids directly or as by-products such as in reactions with HF (fluorination), chlorine and HF (chlorofluorination), chlorine (chlorination), bromine (bromination), hydrogen (such as hydrodechlorination or hydrodefluorination), or with sulfuric acid (such as in HF recovery).

Saturated acyclic fluorinated hydrocarbons of the present invention are compounds represented by the formula $C_aH_bF_cW_dR_e$, wherein a is an integer from 1 to 10, b is an integer at least 1, c is an integer at least 1, d is an integer from 0 to 10, e is an integer from 0 to 4, the sum of b, c, d, and e is equal to 2a+2, and wherein: W is selected from the group consisting of Cl, Br, and I; R is functional group selected from the group consisting of aryl, $C_1$-$C_{12}$ alkyl, $C_1$-$C_{12}$ polyhaloalkyl, $C_2$-$C_{12}$ alkenyl, $C_2$-$C_{12}$ polyhaloalkenyl, $C_2$-$C_{12}$ alkynyl, $C_3$-$C_{12}$ polyhaloalkynyl, $C(O)R^1$, $CO_2R^1$, $C(O)H$, CN, $NO_2$, $OR^1$, $O_2CR^1$, and $SO_2R^1$; and $R^1$ is aryl, $C_1$-$C_6$ alkyl, and $C_1$-$C_6$ polyhaloalkyl.

Saturated cyclic fluorinated hydrocarbons of the present invention are compounds represented by the formula $C_fH_gF_hW_iR_j$, wherein f is an integer from 3 to 6, g is an integer at least 1, h is an integer at least 1, i is an integer from 0 to 10, j is an integer from 0 to 4, the sum of g, h, i, and j is equal to 2f, and W and R are as defined earlier herein for the present saturated acyclic fluorinated hydrocarbons.

Unsaturated acyclic fluorinated hydrocarbons of the present invention are compounds represented by the formula $C_nH_pF_qW_rR_s$, wherein n is an integer from 2 to 6, p is an integer from 0 to 11, q is an integer at least 1, r is an integer from 0 to 8, s is an integer from 0 to 4, the sum of p, q, r, and s is equal to 2n, and W and R are as defined earlier herein for the present saturated acyclic fluorinated hydrocarbons.

Unsaturated cyclic fluorinated hydrocarbons of the present invention are compounds represented by the formula $C_tH_uF_vW_xR_y$, wherein t is an integer from 3 to 6, u is an integer from 0 to 9, v is an integer at least 1, x is an integer from 0 to 8, and y is an integer from 0 to 4, the sum of u, v, x, and y is equal to 2t−2, and where W and R are as defined earlier herein for the present saturated acyclic fluorinated hydrocarbons.

More preferably, the process of the present invention is carried out wherein said at least one fluorinated hydrocarbon is selected from the group consisting of: (i) saturated acyclic fluorinated hydrocarbons of the formula $C_aH_bF_c$, wherein a is an integer from 1 to 10, b is an integer from 1 to 21, c is an integer from 1 to 21, and the sum of b and c is equal to 2a+2, (ii) saturated cyclic fluorinated hydrocarbons of the formula $C_fH_gF_h$, wherein f is an integer from 3 to 6, g is an integer from 1 to 11, h is an integer from 1 to 11, and the sum of g and h is equal to 2f, (iii) unsaturated acyclic fluorinated hydrocarbons of the formula $C_nH_pF_q$, wherein n is an integer from 2 to 6, p is an integer from 0 to 11, q is an integer from 1 to 12, and the sum of p and q is equal to 2n, and (iv) unsaturated cyclic fluorinated hydrocarbons of the formula $C_tH_uF_v$, wherein t is an integer from 3 to 6, u is an integer from 0 to 9, v is an integer from 1 to 10, and the sum of u and v is equal to 2t−2.

The present inventive process is especially suitable for saturated, acyclic or cyclic, fluorinated hydrocarbons having relatively acidic hydrogen substituents. The acidity of the hydrogen substituents is influenced by the presence of electron-withdrawing substitutents, such as halogens or polyhaloalkyl groups such as $CF_3$, in the molecule. Such compounds are characterized by $pK_a$ values in the range of from about 11 to about 25 as discussed by Smart on pages 988 to 989 of *Chemistry of Organic Fluorine Compounds II*, edited by M. Hudlicky and A. E. Pavlath, ACS Monograph 187, American Chemical Society, Washington, D.C. (1995), and by Reutov, Beletskaya, and Butin on pages 51 to 58 in CH-Acids, Pergamon Press, Oxford (1978). These compounds are also characterized by halogen substitution patterns which have vicinal hydrogen and halogen substitutents that allow the possibility of facile elimination of hydrogen halide in the presence of a strong base.

Examples of substitution patterns that promote easy elimination of hydrogen halide in the presence of strong base include acyclic and cyclic compounds having the following structural features:

—CHZCHZ-, —$CZ_2$CHZ-, —$CH_2$CHZ-, —$CZ_2CH_2$—, $CZ_3$CHZ-, and $CZ_3CH_2$— where Z is independently selected from the group consisting of F, Cl, Br, and I. In particular, compounds such as HFC-236fa, HCFC-235fa ($CF_3CH_2CClF_2$), and HFC-245fa which have the structural feature —$CZ_2CH_2CZ_2$-, are surprisingly reactive toward aqueous solutions having a pH greater than about 10.

Representative saturated acyclic fluorinated hydrocarbons of the present invention, compounds that are relatively acidic and susceptible to elimination of HF include, but are not limited to, 1,1,1,2,3,3,3-heptafluoropropane ($CF_3CHFCF_3$, HFC-227ea), 1,1,1,3,3,3-hexafluoropropane ($CF_3CH_2CF_3$, HFC-236fa), 1,1,1,2,3,3-hexafluoropropane ($CF_3CHFCHF_2$, HFC-236ea), 1,1,1,3,3-pentafluoropropane ($CF_3CH_2CHF_2$, HFC-245fa), 1,1,1,2,3-pentafluoropropane ($CF_3CHFCH_2F$, HFC-245eb), 1,1,2,3,3-pentafluoropropane ($CHF_2CHFCHF_2$, HFC-245ea), 1,1,1,3-tetrafluoropropane ($CF_3CH_2CH_2F$, HFC-254fb), 1,1,1,3,3,3-hexafluoro-2-trifluoromethylpropane (($CF_3)_3CH$, HFC-356m/z), 1,1,1,2,2,4,4,4-octafluorobutane ($CF_3CF_2CH_2CF_3$, HFC-338mf, 1,1,1,3,3-pentafluorobutane ($CH_3CF_2CH_2CF_3$, HFC-365mfc), 1,1,1,2,2,3,4,5,5,5-decafluoropentane ($CF_3CHFCHFCF_2CF_3$, HFC-43-10mee), 1,1,1,2,2,4,4,5,5,5-decafluoropentane ($CF_3CF_2CH_2CF_2CF_3$, HFC-43-10mcf), 1,1,1,2,2,3,3,5,5,5-decafluoropentane ($CF_3CH_2CF_2CF_2CF_3$, HFC-43-10mf), and 1,1,1,2,2,3,4,5,5,6,6,7,7,7-tridecafluoroheptane ($CF_3CF_2CHFCHFCF_2CF_2CF_3$, HFC-63-14mcee). Representative saturated cyclic fluorinated hydrocarbons of the present invention, compounds that are relatively acidic and susceptible to elimination of HF include, but are not limited to, 1,1,2,2,3,3,4,4,5-nonafluorocyclopentane (cyclo-$CHFCF_2CF_2CF_2CF_2$—), 1,1,2,2,3,3,4,5-octafluorocyclopentane (cyclo-$CHFCHFCF_2CF_2CF_2$—), 1,1,2,2,3,3,4-heptafluorocyclopentane (cyclo-$CH_2CHFCF_2CF_2CF_2$—).

Representative examples of saturated acyclic fluorinated hydrocarbons of the present invention substituted with other halogens or functional groups which are relatively acidic and susceptible to elimination of HY (hydrogen halide) include, but are not limited to, 1,1,2-trichloro-2,2-difluoroethane ($CHCl_2CClF_2$, HCFC-122), 2,2-dichloro-1,1,1-trifluoroethane ($CHCl_2CF_3$, HCFC-123), 2,3-dichloro-1,1,1,3,3-pentafluoropropane ($CF_3CHClCClF_2$, HCFC-225da), 2-chloro-1,1,1,3,3,3-hexafluoropropane ($CF_3CHClCF_3$, HCFC-226da), 3-chloro-1,1,1,2,3,3-hexafluoropropane ($CF_3CHFCClF_2$, HCFC-226ea), 2,3,3-trichloro-1,1,1-trifluoropropane ($CF_3CHClCHCl_2$, HCFC-233da), 2,3-dichloro-1,1,1,3-tetrafluoropropane ($CF_3CHClCHClF$, HCFC-234da), 3-chloro-1,1,1,3,3-pentafluoropropane ($CF_3CH_2CClF_2$, HCFC-235fa), 2-chloro-1,1,1,3,3-pentafluoropropane ($CF_3CHClCHF_2$, HCFC-235da), 2,3-dichloro-1,1,1-trifluoropropane ($CF_3CHClCH_2Cl$, HCFC-243 db), 3-chloro-1,1,1,3-tetrafluoropropane ($CF_3CH_2CHClF$, HCFC-244fa), 2,3-dibromo-1,1,1,3,3-pentafluoropropane ($CF_3CHBrCBrF_2$), 2,3-dibromo-1,1,1-trifluoropropane ($CF_3CHBrCH_2Br$), 2,3-dibromo-1,1,1,3-tetrafluoropropane ($CF_3CHBrCHBrF$), 1,1,1,2,3,3-hexafluoro-3-methoxypropane ($CF_3CHFCF_2OCH_3$), 1,1,1,2-tetrafluoro-2-methoxyethane ($CF_3CHFOCH_3$), 1,1,2-trifluoro-1-methoxy-2-trifluoromethoxyethane ($CH_3OCF_2CHFOCF_3$), 1,1,1-trifluoro-2-difluoromethoxyethane ($CF_3CH_2OCHF_2$), 1,1,1-trifluoro-2-trifluoromethoxyethane ($CF_3CH_2OCF_3$), 1,1,1,2-tetrafluoro-2-trifluoromethoxyethane ($CF_3CHFOCF_3$), 1,1,1,2-tetrafluoro-2-difluoromethoxyethane ($CF_3CHFOCHF_2$), 2,3,3,3-tetrafluoropropionitrile ($CF_3CHFCN$), and methyl 3,3,3-trifluoropropionate ($CF_3CHFCO_2CH_3$).

Representative acyclic and cyclic unsaturated fluorinated compounds of the present invention, compounds that can undergo nucleophilic attack and/or hydrolysis, include tetrafluoroethylene ($CF_2=CF_2$, TFE), hexafluoropropylene ($CF_3CF=CF_2$, HFP), 1,1,3,3,3-pentafluoro-1-propene ($CF_3CH=CF_2$, HFC-1225zc), 1,1,2,3,3-pentafluoro-1-propene ($CHF_2CF=CF_2$, HFC-1225yc), 2-chloro-1,3,3,3-pentafluoro-1-propene ($CF_3CCl=CF_2$, CFC-1215xc), and hexafluorocyclobutane (cyclo-$C_4F_6$).

The process of the present invention is also useful for reducing the concentration of acidic contaminants from a mixture comprising saturated and unsaturated fluorinated hydrocarbons without substantial degradation of said saturated and unsaturated fluorinated hydrocarbons. Examples of mixtures of saturated hydrofluorocarbons and unsaturated fluorinated hydrocarbons which may be treated to remove acidic contaminants by the process of this invention include, but are not limited to, mixtures of HFC-227ea and HFP, mixtures of HFC-236fa and HFC-1225zc, mixtures of HFC-236ea and HFC-1225ye, mixtures of HFC-245fa and HFC-1234ze ($CF_3CH=CHF$), mixtures of HFC-227ea, HFC-236fa, HFP, and HFC-1225zc, mixtures of HFC-227ea, HFC-245fa, HFP, and HFC-1234ze, and mixtures of HFC-236fa, HFC-245fa, HFC-1234ze, and HFC-1225zc.

The present invention is also suitable for removing acidic contaminants from mixtures of saturated and/or unsaturated fluorinated hydrocarbons in which the acidic contaminants are present as an azeotrope with one or more of the fluorinated hydrocarbons. Examples of azeotropes of inorganic acids and fluorinated hydrocarbons which may be treated to remove the acidic contaminant by the process of this invention include, but are not limited to, the HF azeotrope of HFC-227ea as described in U.S. Pat. No. 6,376,727, the HF azeotrope of HFC-236ea as described in U.S. Pat. No. 5,563,304, the HF azeotrope of HFC-236fa as described in U.S. Pat. No. 5,563,304, the HF azeotrope of HCFC-235fa as described in U.S. Pat. No. 6,291,730, and the HF azeotrope of HFC-245fa as described in U.S. Pat. No. 6,291,730.

The contacting step of the present invention in which a mixture containing one or more fluorinated hydrocarbons and one or more acidic contaminants is contacted with an aqueous solution of salts of phosphorous oxyacids may be accomplished by any one of several methods using well-known chemical engineering practices for scrubbing organic compounds. This step may be carried out in batch or continuous mode. In one embodiment of the invention, the mixture containing the acid-contaminated fluorinated hydrocarbon may be contacted with the aqueous solution under a suitable amount of pressure to maintain a liquid phase of the fluorinated hydrocarbon in the contacting vessel. The contents of the vessel may be agitated to provide contact between the aqueous solution and the fluorinated hydrocarbon. The fluorinated hydrocarbon is then collected as a lower layer from the vessel or recovered by distillation.

In another embodiment of the present process, the mixture containing the acid-contaminated fluorinated hydrocarbon may be bubbled into the aqueous solution as a gas in a stirred tank reactor. The fluorinated hydrocarbon is then allowed to leave the reactor, optionally through a condenser, where it is collected for subsequent purification.

In a preferred embodiment of the present invention, the contacting step is conducted in a column packed with materials such as helices, rings, saddles, spheres or other formed shapes fabricated from glass, plastic, or ceramics. The mixture of fluorinated hydrocarbon(s) and acidic contaminant(s) enters the bottom of the column as a vapor. The aqueous solution enters the top of the column, for example, by means of a pump connected to a reservoir of said aqueous solution. The acidic contaminant(s) in the fluorinated hydrocarbon then reacts with the aqueous solution in the column and the fluorinated hydrocarbon vapor, with reduced acidic contaminant, passes out the top of the column and is then collected. The aqueous solution passes out the bottom of the column and returns to the reservoir.

The aqueous solution may be used until its pH drops to a pre-determined point typically from about 6 to about 7. The aqueous solution is then replaced or treated with additional base, such as potassium hydroxide, to bring the pH to the desired value. The restoration of the pH may continue until the concentration of salts in the aqueous solution reaches the desired value, usually not to exceed about 20 weight percent.

The pressure during the contacting steps is not critical, though atmospheric and superatmospheric pressures are preferred. Operating the process under pressure may be advantageous for subsequent purification steps such as distillations.

The temperature during the contacting step of the mixture containing the fluorinated hydrocarbon(s) and acidic contaminant(s) with the aqueous solution of phosphorous oxyacid salts is not critical and may take place at temperatures of from about 0° C. to about 100° C., preferably from about 25° C. to about 80° C. Lower temperatures than about 25° C. may result in loss of fluorinated hydrocarbon due to condensation or to solubility in the aqueous phase. Temperatures higher than about 80° C. increase the rate of undesirable elimination processes as observed by increased levels of unsaturated impurities in the fluorinated hydrocarbon and increased levels of halide ion (e.g., fluoride) in the aqueous phase.

The time of contact between the mixture of the fluorinated hydrocarbon and the aqueous solution is not critical and typically may be on the order of about 30 seconds to about an hour. In the preferred embodiment of the invention, the contact time may be typically from about 30 seconds to about 10 minutes.

In the recovering step of the process of the present invention, fluorinated hydrocarbon product(s) that has been freed of the acid contaminant(s) is delivered to a separation unit for recovery. The fluorinated hydrocarbon product will typically be separated from water by means of a decanter, by distillation, or by drying with a molecular sieve or anhydrous salt (for example, calcium sulfate), or by a combination thereof. The fluorinated hydrocarbon product may then be further purified by distillation.

Without further elaboration, it is believed that one skilled in the art can, using the description herein, utilize the present invention to its fullest extent. The following specific embodiments are, therefore, to be construed as merely illustrative, and do not constrain the remainder of the disclosure in any way whatsoever.

EXAMPLES

| LEGEND | |
|---|---|
| 123 is $CF_3CHCl_2$ | 225da is $CF_3CHClCClF_2$ |
| 227ea is $CF_3CHFCF_3$ | 235fa is $CF_3CH_2ClF_2$ |
| 236ea is $CF_3CHFCHF_2$ | 236fa is $CF_3CH_2CF_3$ |
| 245fa is $CF_3CH_2CHF_2$ | 365mfc is $CF_3CH_2CF_2CH_3$ |
| 43-10mee is $CF_3CHFCHFCF_2CF_3$ | 1225zc is $CF_3CH=CF_2$ |
| HFP is $CF_3CF=CF_2$ | |

Preparation of Solutions of Aqueous Bases

Preparation of 6.5:1 $Na_2HPO_4/NaH_2PO_4$ Solutions

A 20 wt % stock solution of 6.5:1 $Na_2HPO_4/NaH_2PO_4$ (mole basis) was prepared by adding 14.90 g (0.09552 mole) $NaH_2PO_4[2(H_2O)]$ and 88.55 g (0.6238 mole) $Na_2HPO_4$ to a flask and bringing the total weight to 500.0 g with deionized water. The solution was 2.29 wt % $NaH_2PO_4$ (based on the anhydrous salt) and 17.71 wt % $Na_2HPO_4$. The 20% buffer stock solution prepared above was then diluted 1 to 5 by weight with water to give a 4 wt % buffer solution (3.54 wt % $Na_2HPO_4$, 0.458 wt % $NaH_2PO_4$) having a pH of 7.54.

Preparation of 5.7:1 $K_2HPO_4/KH_2PO_4$ Solutions 136.4 g (1.193 mole) of $H_3PO_4$ (85.7%) was diluted with 400.7 g of water in a large Erlenmeyer flask. The resulting acid solution was treated dropwise with 412.9 g (2.208 mole) of 30 wt % KOH (prepared by dissolving 171.8 g of 87.3% KOH pellets in 328.2 g of DI water). The addition funnel was rinsed into the final solution with an additional 50.0 g of water. The resulting solution is about 17.7 wt % $K_2HPO_4$ and 2.4 wt % $KH_2PO_4$. A 4 wt % potassium phosphate buffer solution was prepared by diluting the 20 wt % buffer 1 to 5 with water; the pH of the solution was 7.43.

Preparation of 6:1 $K_2HPO_4/KH_2PO_4$ Solutions 17.70 g (0.102 mole) of $K_2HPO_4$ and 2.30 g (0.0169 mole) of $KH_2PO_4$ were dissolved in water and brought to a total weight of 100 g. The resulting solution was diluted 1 to 5 with water to give a 4% (w/w) solution having a pH of 7.92.

Preparation of 98:2 $K_2HPO_4/K_3PO_4$ Solutions 19.515 g (0.112 mole) of $K_2HPO_4$ and 0.485 g (0.00228 mole) of $K_3PO_4$ were dissolved in water and brought to a total weight of 100 g. The resulting solution was diluted 1 to 5 with water to give a 4% (w/w) solution having a pH of 9.93.

Preparation of 1:1 $K_2HPO_4/K_3PO_4$ Solutions 9.015 g (0.0518 mole) of $K_2HPO_4$ and 10.985 g (0.0517 mole) of $K_3PO_4$ were dissolved in water and brought to a total weight of 100 g. The resulting solution was diluted 1 to 5 with water to give a 4% (w/w) solution having a pH of 11.86.

Preparation of 6% $Na_2CO_3$/3% $Na_2SO_3$ Solution 10.5 g (0.0991 mole) of $Na_2CO_3$ and 5.25 g (0.0417 mole) of $Na_2SO_3$ were dissolved in water (159.25 g). The pH of the resulting solution was 11.63.

Preparation of 2% $Na_2CO_3$ Solution 3.5 g (0.0330 mole) of $Na_2CO_3$ were dissolved in water (171.5 g). The pH of the resulting solution was 11.49.

Preparation of 2% $Na_2SO_3$ Solution 3.5 g (0.0278 mole) of $Na_2SO_3$ were dissolved in water (171.5 g). The pH of the resulting solution was 10.04.

General Procedure for Assessing Reactivity of Hydrofluorocarbons with Basic Aqueous Solutions The reactivity of various hydrofluorocarbons with bases was assessed by contacting a mixture of the two in sealed tubes (shaker tubes) or in a counter-current scrubber at a specified temperature for a specified period of time. The recovered hydrofluorocarbon was analyzed by GC. The recovered aqueous phases was weighed, purged with nitrogen to expel any dissolved hydrofluorocarbon, and the pH determined. The chloride ion concentration in the aqueous phase was determined by means of ion selective electrode. The fluoride ion concentration in the aqueous phase was determined by means of an ion selective electrode or ion chromatography using authentic fluoride standards to calibrate the methods. Time average rates of decomposition of the fluorocarbons were based on the concentrations of fluoride in the aqueous phase and the time of agitation of the shaker tube or the time of fluorinated hydrocarbon gas flow through the counter-current scrubber.

General Procedure for Shaker Tube Tests

A 400 mL stainless steel shaker tube was charged with 175.0 g of aqueous base. The shaker tube was sealed, cooled in dry ice, evacuated, and purged with nitrogen. The tube was re-evacuated and charged with 25.0 g of hydrofluorocarbon. The tube was then placed in the shaker mechanism and brought to the desired temperature with agitation. It generally took 1-1.5 hours to bring the cold tube to the temperature set point. The tube was then held at the desired temperature (either 40° C. or 100° C.) for 0.5 hour. After 0.5 hour, agitation was ceased and the tube was cooled in a stream of air. It typically took at least 0.5 hour to cool the tube. If the hydrofluorocarbon was a gas at room temperature, it was collected in an evacuated 300 mL cylinder chilled in dry ice. If the hydrofluorocarbon was a liquid at room temperature, it was discharged with the aqueous phase from the shaker tube and then separated as a liquid.

The results of contacting several fluorinated hydrocarbons with basic solutions in shaker tubes are given in Table 1. "C" (e.g., C1) example numbers are comparative examples.

General Procedure for Counter-Current Scrubber Tests

The counter-current scrubber consisted of an 46 cm×2.5 cm i.d. Pyrex™ glass tube packed with 7×7 mm Raschig rings connected to a 5 L flask which served as a reservoir for the scrubbing medium. A variable speed peristaltic pump circulated the scrubbing solution from the reservoir to the top of the column. The test gas entered the vapor space of the reservoir and moved up through the packed column where it contacted the basic media. The scrubbed hydrofluorocarbon gas passed through a drying tube packed with anhydrous calcium sulfate and condensed in a cylinder immersed in dry ice.

The reservoir was charged with about 1 kg of scrubbing media. The reactor system was purged with nitrogen at 100 sccm ($1.7 \times 10^{-6}$ m$^3$/s) with the pump feeding caustic at 100 mL/min while the temperature of the caustic in the reservoir was brought to temperature (typically 60±2° C.). The nitrogen flow was then replaced with the fluorocarbon at a flow rate of 100 sccm ($1.7 \times 10^{-6}$ m$^3$/s). Hydrofluorocarbon was fed to the scrubber for 2 to 3 hours; the pressure in the system was about two inches of water (0.0049 atm). The hydrofluorocarbon flow was then stopped and the system purged with nitrogen while the caustic recirculation rate was increased to about 400 mL/min. The contents of the reservoir were then discharged, weighed, the pH measured, and analyzed for fluoride ion content. The hydrofluorocarbon recovered in the collection cylinder was analyzed by GC-MS. The results of contacting HFC-236fa and HFC-245fa with basic solutions in a counter-current scrubber are given in Table 2. "C" (e.g., C1) example numbers are comparative examples.

TABLE 1

Alkaline Hydrolysis of Fluorinated Hydrocarbons in Shaker Tubes$^a$

| Example No. | Substrate$^b$ | Scrubbing Media$^c$ | Temperature/ Time$^d$ ° C./hours | Aqueous Phase$^e$ ppm Cl | Aqueous Phase$^e$ ppm F | Average % Decomposition Per Hour$^f$ | % Unsaturates in Fluorinated Hydrocarbon$^g$ |
|---|---|---|---|---|---|---|---|
| 1 | 123 | 6% NaH$_2$PO$_4$ | 50/8 | 7.7 | 0.5 | 0.0032 | nd$^k$ |
| C1 | 123 | 6% Na$_2$CO$_3$/ 3% Na$_2$SO$_3$ | 50/2 | 19200 | <1000 | 33.1 | 15 |
| C2 | 123 | 6% KOH | 50/2 | 28900 | 1500 | 49.8 | 86 |
| 2 | 225da | 6% NaH$_2$PO$_4$ | 50/8 | 116 | 8.6 | 0.057 | 0.3 |
| C3 | 225da | 6% Na$_2$CO$_3$/ 3% Na$_2$SO$_3$ | 50/2 | 22800 | 4300 | 47.6 | 94 |
| C4 | 225da | 6% KOH | 50/2 | 20000 | 4400 | 41.2 | 27 |
| 3 | 227ea | 3.54% K$_2$HPO$_4$/ 0.46% KH$_2$PO$_4$ | 40/0.5 | nd | 2.0 | 0.025$^h$ | 0.0008 |
| 4 | 227ea | 3.54% K$_2$HPO$_4$/ 0.46% KH$_2$PO$_4$ | 100/0.5 | nd | 1.7 | 0.021$^h$ | 0.046 |
| C5 | 227ea | 5% KOH | 40/0.5 | nd | 49.1 | 0.61$^h$ | 0.011 |
| C6 | 227ea | 5% KOH | 100/0.5 | nd | 10440 | 21.9$^i$ | 0.29 |
| 5 | 235fa | 6% NaH$_2$PO$_4$ | 50/8 | 1.2 | 0.1 | 0.000041 | 0.06 |
| 6 | 235fa | 4% KH$_2$PO$_4$ | 80/0.5 | 32 | <0.5 | 0.21 | nd |
| C7 | 235fa | 6% Na$_2$CO$_3$/ 3% Na$_2$SO$_3$ | 25/4 | 833 | 700 | 0.68 | 0.12 |
| C8 | 235fa | 2% Na$_2$CO$_3$ | 40/0.5 | 1219 | 161 | 8.0 | 0.58 |
| C9 | 235fa | 2% Na$_2$SO$_3$ | 40/0.5 | 1066 | 102 | 7.0 | 0.34 |
| 7 | 236ea | 6% NaH$_2$PO$_4$ | 50/8 | nd | 0.1 | 0.000069 | not measured |
| 8 | 236ea | 3.54% K$_2$HPO$_4$/ 0.46% KH$_2$PO$_4$ | 40/0.5 | nd | 0.75 | 0.0082 | 0.05 |
| C10 | 236ea | 6% Na$_2$CO$_3$/ 3% Na$_2$SO$_3$ | 50/2 | nd | 52 | 0.14 | not measured |
| C11 | 236ea | 5% KOH | 40/0.5 | nd | 625 | 6.87 | 3. |
| 9 | 236fa | 4% KH$_2$PO$_4$ | 80/0.5 | 2.0 | <0.5 | 0.0055$^h$ | 0.003 |
| 10 | 236fa | 2% Na$_2$HPO$_4$/ 2% KH$_2$PO$_2$ | 80/0.5 | 14.0 | <0.5 | 0.0055$^h$ | 0.0047 |
| C12 | 236fa | 6% Na$_2$CO$_3$/ 3% Na$_2$SO$_3$ | 25/4 | nd | 18.8 | 0.0043$^i$ | 0.023 |
| C13 | 236fa | 6% Na$_2$CO$_3$/ 3% Na$_2$SO$_3$ | 50/2 | nd | 71.9 | 0.033$^i$ | 0.085 |
| C14 | 236fa | 2% Na$_2$CO$_3$ | 80/0.5 | <5.0 | 578 | 1.1$^i$ | 1.6 |
| C15 | 236fa | 5% KOH | 40/0.5 | nd | 2330 | 4.3$^i$ | 0.4 |
| 11 | 245fa | 3.54% K$_2$HPO$_4$/ 0.46% KH$_2$PO$_4$ | 40/0.5 | nd | 1.4 | 0.0135 | 0.48 |
| 12 | 245fa | 3.54% K$_2$HPO$_4$/ 0.46% KH$_2$PO$_4$ | 100/0.5 | nd | 37 | 0.357 | 0.63 |
| C16 | 245fa | 5% KOH | 40/0.5 | nd | 958 | 9.27 | 4.7 |
| C17 | 245fa | 5% KOH | 100/0.5 | nd | 14752 | 145.7 | 73 |
| 13 | HFP | 3.54% K$_2$HPO$_4$/ 0.46% KH$_2$PO$_4$ | 40/0.5 | nd | 9.1 | 0.049 | nd |
| 14 | HFP | 3.54% K$_2$HPO$_4$/ 0.46% KH$_2$PO$_4$ | 100/0.5 | nd | 854 | 4.64 | nd |
| C18 | HFP | 5% KOH | 40/0.5 | nd | 9640 | 54.8 | nd |
| C19 | HFP | 5% KOH | 100/0.5 | nd | 8750 | 49.5 | nd |
| 15 | 1225zc | 6% NaH$_2$PO$_4$ | 50/8 | 63 | 2.5 | 0.00073$^h$ | nd |

TABLE 1-continued

Alkaline Hydrolysis of Fluorinated Hydrocarbons in Shaker Tubes[a]

| Example No. | Substrate[b] | Scrubbing Media[c] | Temperature/ Time[d] ° C./hours | Aqueous Phase[e] ppm Cl | Aqueous Phase[e] ppm F | Average % Decomposition Per Hour[f] | % Unsaturates in Fluorinated Hydrocarbon[g] |
|---|---|---|---|---|---|---|---|
| 16 | 1225zc | 3.54% $K_2HPO_4$/ 0.46% $KH_2PO_4$ | 40/0.5 | nd | 9.0 | 0.043[h] | nd |
| 17 | 1225zc | 3.54% $K_2HPO_4$/ 0.46% $KH_2PO_4$ | 100/0.5 | nd | 990 | 4.8[h] | nd |
| C20 | 1225zc | 6% $Na_2CO_3$/ 3% $Na_2SO_3$ | 25/4 | 173 | 5650 | 1.4[i] | nd |
| C21 | 1225zc | 5% KOH | 40/0.5 | nd | 9880 | 19.5[i] | nd |
| 18 | 365mfc | 3.54% $K_2HPO_4$/ 0.46% $KH_2PO_4$ | 40/0.5 | nd | 13 | 0.14 | j |
| 19 | 365mfc | 3.54% $K_2HPO_4$/ 0.46% $KH_2PO_4$ | 100/0.5 | nd | 5 | 0.054 | 0.08 |
| C22 | 365mfc | 5% KOH | 40/0.5 | nd | 350 | 3.85 | 0.49 |
| C23 | 365mfc | 5% KOH | 100/0.5 | nd | 14,130 | 158 | 53 |
| 20 | 43-10mee | 3.54% $K_2HPO_4$/ 0.46% $KH_2PO_4$ | 40/0.5 | nd | 8.0 | 0.15 | 0.015 |
| C24 | 43-10mee | 5% KOH | 40/0.5 | nd | 5,000 | 91.4 | 46 |

[a]Reactions conducted in 400 mL Hastelloy™ C or stainless steel shaker tubes using 25.0 g of fluorinated hydrocarbon and 175 g of aqueous scrubbing media. Blank runs typically contained 1.3 ppm chloride and 1 ppm fluoride.
[b]Fluorocarbon fed to scrubber; see Legend.
[c]Type of aqueous caustic solution used in shaker tube. Percentages are on a weight basis.
[d]Temperature in shaker tube during hold period and duration of hold period in hours. Typically took 1-1.5 hours to warm the shaker tube from the starting temperature of about −20° C. to the reaction temperature, and about 0.5 hour to cool the tube to ambient temperature after the run.
[e]Concentration of halide in parts per million (weight) in the recovered aqueous phase at the end of the reaction period.
[f]Average Rate of Decomposition per Hour = [(Halide concn.)(Wt. Aq. Soln)(100)]/[(f)(moles fluorocarbon)(At. Wt.)(Time, hours)] where Halide concentration = ppm halide/1 × $10^6$; Wt. Aq. Soln = total weight of aqueous phase recovered from tube f = stoichiometry factor; f = 6 for 236fa and 227ea, f = 5 for 1225zc, f = 2 for HFP, f = 3 for 226da, f = 1 for all other fluorocarbons; moles fluorocarbon = (Wt. Fluorocarbon fed, grams)/Mol. Wt.); At. Wt. = atomic weight of halide. Decomposition rates based on chloride analysis for HCFC-122, -225da, and -235fa; fluoride analysis used for all others.
[g]GC area percentage of unsaturated product(s) in the recovered fluorinated hydrocarbon.
[h]Maximum value of decomposition rate. For most fluorocarbons, this assumes one mole of fluorocarbon decomposes to give one mole of fluoride (f = 1). For HFP and HFC-1225zc the maximum value assumes one mole of the fluoropropene gives a minimum of two moles of fluoride.
[i]Minimum value of decomposition rate. This assumes that decomposition of one mole of 1225zc, 236fa, or 227ea yields 5, 6, or 6 moles of fluoride, respectively.
[j]The concentration of unsaturates was about the same as in the starting HFC-365mfc.
[k]nd = not detected

TABLE 2

Alkaline Hydrolysis of Fluorinated Hydrocarbons in Counter-current Scrubbers[a]

| Example No. | Substrate[b] | Scrubbing Media[c] | pH[d] | Fluoride Level[e] (ppm) | Average % Decomposition Per Hour[f] | % Unsaturate in Fluorinated Hydrocarbon[g] |
|---|---|---|---|---|---|---|
| C25 | 236fa | 5% NaOH | 13.09 | 1380 | 0.50 | 0.066 |
| 21 | 236fa | 4% 1:1 $K_2HPO_4$:$K_3PO_4$ | 11.89 | 120 | 0.044 | 0.038 |
| 22 | 236fa | 4% 98:2 $K_2HPO_4$:$K_3PO_4$ | 9.65 | 1 | 0.00038 | 0.017 |
| 23 | 236fa | 4% 6:1 $K_2HPO_4$:$KH_2PO_4$ | 7.83 | 0.5 | 0.00017 | 0.019 |
| C26 | 245fa[h] | 5% NaOH | 13.8 | 1497 | 8.5 | 16.6 |
| 24 | 245fa[h] | 4% 98:2 $K_2HPO_4$:$K_3PO_4$ | 9.88 | 11.4 | 0.062 | 0.14 |
| 25 | 245fa[h] | 4% 6:1 $K_2HPO_4$:$KH_2PO_4$ | 7.64 | 4.1 | 0.016 | 0.24 |

[a]All reactions were conducted in a counter-current reactor. The fluorocarbon feed rate was 100 sccm and the caustic flow rate was 100 mL/min. The reactions were run for 3 hours at 60° C. unless indicated otherwise.
[b]Fluorocarbon fed to scrubber; see Legend.
[c]Type of aqueous caustic solution used in counter-current reactor. Percentages are on a weight basis; ratios are on a molar basis.
[d]Initial pH of solution of aqueous base in the reservoir.
[e]Concentration of fluoride in parts per million (weight) in the caustic reservoir at the end of the reaction period.
[f]Average Rate of Decomposition per Hour = [(Fluoride level)(Wt. Aq. Soln)(100)]/[(f)(moles fluorocarbon)(19)(Time, hours)] where: Fluoride level = ppm fluoride/1 × $10^6$; Wt. Aq. Soln = total weight of recovered caustic from reservoir; f = stoichiometry factor; f = 6 for 236fa and 227ea, f = 5 for 1225zc and HFP; f = 1 for 245fa; moles fluorocarbon = (Wt. Fluorocarbon fed)/(Mol. Wt.); 19 = atomic weight of fluorine; Run time = 3 hours
[g]GC area percentage of unsaturated product(s) in the recovered fluorinated hydrocarbon
[h]Run time was 2 hours.

What is claimed is:

1. A process for reducing the concentration of at least one acidic contaminant selected from the group consisting of HF, HBr, HI, $HNO_3$ or $H_2SO_4$ in a mixture of at least one fluorinated hydrocarbon and said at least one acidic contaminant, comprising:

contacting said mixture with substantially dry phosphorous oxyacid salt, at temperatures of from about 0° C. to about 100° C., and recovering said at least one fluorinated hydrocarbon having reduced concentration of said at least one acidic contaminant.

2. The process of claim 1 wherein said substantially dry phosphorous oxyacid salt is in a bed.

3. The process of claim 1 wherein the substantially dry phosphorous oxyacid salt is in an agitated bed.

4. The process of claim 1 wherein said at least one fluorinated hydrocarbon is selected from the group consisting of:

(i) saturated acyclic fluorinated hydrocarbons of the formula $C_aH_bF_cW_dR_e$, wherein a is an integer from 1 to 10, b is an integer at least 1, c is an integer at least 1, d is an integer from 0 to 10, e is an integer from 0 to 4, and the sum of b, c, d, and e is equal to 2a+2, (ii) saturated cyclic fluorinated hydrocarbons of the formula $C_fH_gF_hW_iR_j$, wherein f is an integer from 3 to 6, g is an integer at least 1, h is an integer at least 1, i is an integer from 0 to 10, j is an integer from 0 to 4, and the sum of g, h, i, and j is equal to 2f, (iii) unsaturated acyclic fluorinated hydrocarbons of the formula $C_nH_pF_qW_rR_s$, wherein n is an integer from 1 to 6, p is an integer from 0 to 11, q is an integer at least 1, r is an integer from 0 to 8, s is an integer from 0 to 4, and the sum of p, q, r, and s is equal to 2n, and (iv) unsaturated cyclic fluorinated hydrocarbons of the formula $C_tH_uF_vW_xR_y$, wherein t is an integer from 3 to 6, u is an integer from 0 to 9, v is an integer at least 1, x is an integer from 0 to 8, y is an integer from 0 to 4, and the sum of u, v, x, and y is equal to 2t−2, wherein: W is selected from the group consisting of Cl, Br, and I; R is selected from the group consisting of aryl, $C_1$-$C_{12}$ alkyl, $C_1$-$C_{12}$ polyhaloalkyl, $C_2$-$C_{12}$ alkenyl, $C_2$-$C_{12}$ polyhaloalkenyl, $C_2$-$C_{12}$ alkynyl, $C_3$-$C_{12}$ polyhaloalkynyl, $C(O)R^1$, $CO_2R^1$, $C(O)H$, $CN$, $NO_2$, $OR^1$, $O_2CR^1$, and $SO_2R^1$; and $R^1$ is selected from the group consisting of aryl, $C_1$-$C_6$ alkyl, and $C_1$-$C_6$ polyhaloalkyl.

5. The process of claim 4 wherein said at least one fluorinated hydrocarbon is selected from the group consisting of:

(i) saturated acyclic fluorinated hydrocarbons of the formula $C_aH_bF_c$, wherein a is an integer from 1 to 10, b is an integer from 1 to 21, c is an integer from 1 to 21, and the sum of b and c is equal to 2a+2, (ii) saturated cyclic fluorinated hydrocarbons of the formula $C_fH_gF_h$, wherein f is an integer from 3 to 6, g is an integer from 1 to 11, h is an integer from 1 to 11, and the sum of g and h is equal to 2f, (iii) unsaturated acyclic fluorinated hydrocarbons of the formula $C_nH_pF_q$, wherein n is an integer from 2 to 6, p is an integer from 0 to 11, q is an integer from 1 to 12, and the sum of p and q is equal to 2n, and (iv) unsaturated cyclic fluorinated hydrocarbons of the formula $C_tH_uF_v$, wherein t is an integer from 3 to 6, u is an integer from 0 to 9, v is an integer from 1 to 10, and the sum of u and v is equal to 2t−2.

6. The process of claim 5 wherein said at least one fluorinated hydrocarbon is $CF_3CH_2CHF_2$.

7. The process of claim 1 wherein said phosphorous oxyacid salt is selected from the group consisting of:

(i) orthophosphoric acid salts of the formula $M_nH_{3-n}PO_4$, wherein n is an integer from 1 to 3,;

(ii) phosphorous acid salts of the formula $M_mH_{2-m}(HPO_3)$, wherein m is 1 or 2;

(iii) metaphosphoric acid salts of the formula $(MPO_3)_z$, wherein z is an integer from 1 to 6; and (iv) pyrophosphoric acid salts of the formula $M_kH_{4-k}P_2O_7$, wherein k is an integer from 1 to 4, wherein M is selected from the group consisting of $NH_4$, Li, Na, and K.

8. The process of claim 7 wherein said phosphorous oxyacid salt is an orthophosphoric acid salt of the formula $M_nH_{3-n}PO_4$, wherein n is an integer from 1 to 3, and M is selected from the group consisting of $NH_4$, Na, and K.

9. The process of claim 1 whereby less than about 5 weight percent of said at least one fluorinated hydrocarbon is decomposed by dehydrohalogenation or hydrolysis during said contacting step.

10. The process of claim 1 wherein said mixture is azeotropic or azeotrope-like.

11. The process of claim 1 wherein said temperatures are from about 25° C. to about 80° C.

* * * * *